US012802182B2

(12) United States Patent
Van Den Dungen et al.

(10) Patent No.: US 12,802,182 B2
(45) Date of Patent: Nov. 17, 2026

(54) PERSONAL CARE DEVICES

(71) Applicant: KONINKLIJKE PHILIPS N.V., Eindhoven (NL)

(72) Inventors: Wilhelmus Andreas Marinus Arnoldus Maria Van Den Dungen, Boxtel (NL); Mark Thomas Johnson, Arendonk (BE)

(73) Assignee: KONINKLIJKE PHILIPS N.V.

( * ) Notice: Subject to any disclaimer, the term of this patent is extended or adjusted under 35 U.S.C. 154(b) by 213 days.

(21) Appl. No.: 18/722,206

(22) PCT Filed: Dec. 8, 2022

(86) PCT No.: PCT/EP2022/084883
§ 371 (c)(1),
(2) Date: Jun. 20, 2024

(87) PCT Pub. No.: WO2023/117437
PCT Pub. Date: Jun. 29, 2023

(65) Prior Publication Data

US 2025/0131541 A1 Apr. 24, 2025

(30) Foreign Application Priority Data

Dec. 23, 2021 (EP) .................................... 21217425

(51) Int. Cl.
*G06T 5/77* (2024.01)
*A46B 13/02* (2006.01)
(Continued)

(52) U.S. Cl.
CPC .............. *G06T 5/77* (2024.01); *A46B 13/023* (2013.01); *A46B 15/0002* (2013.01); *A61B 1/24* (2013.01);
(Continued)

(58) Field of Classification Search
CPC ............. G06T 5/77; G06T 2207/30036; G06T 2207/30168; G06T 7/002; G06T 7/0012;
(Continued)

(56) References Cited

U.S. PATENT DOCUMENTS 10,896,487 B2 1/2021 Choi
2015/0107034 A1* 4/2015 Shani ................. A46B 15/0006 15/22.1
(Continued)

FOREIGN PATENT DOCUMENTS

CN 107307840 A * 11/2017 ............... A61B 1/05
CN 110856667 A * 3/2020 ............. A61C 17/34
(Continued)

OTHER PUBLICATIONS

International Search Report and Written Opinion of PCT/EP2022/084883, dated Apr. 11, 2023.

*Primary Examiner* — Jose L Couso

(57) ABSTRACT

Proposed are schemes, solutions, concepts, designs, methods and systems pertaining to aiding and/or improving image acquisition from a vibratory personal care device having a camera. Embodiments propose identifying image data captured during a target part (e.g. low velocity/motion part) of the vibration cycle based on an edge quality value of the image data. Using the identified image data, an image of improved quality may then be constructed. Thus, through adaptation of image data acquisition according to edge quality of image data, improved images (e.g. images exhibiting less blur and/or distortion) may be constructed/generated.

9 Claims, 6 Drawing Sheets

(51) Int. Cl.

| | |
|---|---|
| ***A46B 15/00*** | (2006.01) |
| ***A61B 1/24*** | (2006.01) |
| ***A61C 17/34*** | (2006.01) |
| ***G06V 10/26*** | (2022.01) |
| ***G06V 10/44*** | (2022.01) |
| ***G06V 10/75*** | (2022.01) |
| ***G06V 10/98*** | (2022.01) |

(52) U.S. Cl.
CPC .......... *A61C 17/3481* (2013.01); *G06V 10/26* (2022.01); *G06V 10/44* (2022.01); *G06V 10/75* (2022.01); *G06V 10/993* (2022.01)

(58) Field of Classification Search
CPC .............. A46B 13/023; A46B 15/0002; A46B 2200/1066; A46B 15/0036; A46B 15/00; A46B 15/002; A46B 15/0016; A46B 15/0038; A61B 1/24; A61B 1/00066; A61B 1/00131; A61B 1/04; A61C 17/3481; A61C 9/0053; A61C 17/221; A61C 9/004; A61C 17/16; A61C 17/34; A61C 9/0046; A61C 9/0066; A61C 17/26; A61C 19/00; A61C 19/04; A61C 2204/00; G06V 10/26; G06V 10/44; G06V 10/75; G06V 10/993; G06V 20/50; G06V 10/764; G16H 30/40; H04N 23/683; H04N 23/6812; H04N 23/555; H04N 23/80; H04N 23/6845; H04N 23/951
See application file for complete search history.

(56) References Cited

U.S. PATENT DOCUMENTS

| | | | | |
|---|---|---|---|---|
| 2017/0069083 | A1* | 3/2017 | Vetter ................ | A46B 15/0006 |
| 2018/0125610 | A1 | 5/2018 | Carrier, Jr. | |
| 2021/0019885 | A1 | 1/2021 | Jeanne | |
| 2021/0045852 | A1 | 2/2021 | Atiya | |
| 2021/0158607 | A1 | 5/2021 | Katzman | |
| 2021/0393026 | A1* | 12/2021 | Subhash ............ | A46B 15/0034 |
| 2023/0396745 | A1 | 12/2023 | Rmaile | |

FOREIGN PATENT DOCUMENTS

| | | | | | |
|---|---|---|---|---|---|
| CN | 111888025 | A | * | 11/2020 | ............. A61C 17/34 |
| CN | 109567971 | B | * | 7/2021 | ............. G16H 30/40 |
| CN | 113244009 | A | * | 8/2021 | ............. A61C 19/00 |
| CN | 214259544 | U | * | 9/2021 | ............. A61C 19/00 |
| CN | 214761568 | U | * | 11/2021 | ............. A61C 19/00 |

* cited by examiner

PERSONAL CARE DEVICES

This application is the U.S. National Phase application under 35 U.S.C. § 371 of International Application No. PCT/EP2022/084883, filed on Dec. 8, 2022, which claims the benefit of European Application Serial No. 21217425.4, filed Dec. 23, 2021. These applications are hereby incorporated by reference herein.

FIELD OF THE INVENTION

The present invention relates to the field of personal care devices, and in particular to the field of personal care devices that capture digital impressions of one or more features of a user.

BACKGROUND OF THE INVENTION

It is known to provide personal care devices with the ability or functionality to capture digital impressions (e.g. images) of a feature or part of a user during use. For example, Intra-Oral Scanner (IOS) devices use projected light (e.g. laser or structured light) and an image sensor to capture images of the dentogingival tissues. These images can be processed to create a three-dimensional (3D) model of the scanned surface. Data provided by IOS can therefore be useful for oral care, including the detection of common dental pathologies such as caries, tooth discoloration, misalignment. Also, it may be advantageous to capture and compare repeated IOS images, to enable identification of changes in dentogingival tissues over time for example.

Because personal care devices, such as electric brushing or shaving devices, are used on a regular (e.g. daily) basis, they may provide a suitable vehicle to regularly capture images of a user. Accordingly, there is trend to integrate cameras or imaging sensors into personal care devices, such as toothbrushes for example. However, because a main usage characteristic of a personal care device may be its vibration or cyclical/periodic movement, images acquired by a camera integrated with a personal care device are typically distorted and/or blurred by the movement/vibration of the device.

Although image stabilization techniques are known for portable handheld devices (e.g. smart phone, digital photo cameras, etc.), such techniques are only designed and optimized for low frequency (e.g. <10 Hz), erratic (e.g. non-periodic, random, etc.) user-induced motions. Because a personal care device (such as a toothbrush) typically moves or vibrates at a much higher periodic frequency (e.g. >20-300 Hz), there remains a need to stabilize the image capture process and/or make the image acquisition process robust to device movements/vibrations generated by a personal care device.

SUMMARY OF THE INVENTION

The invention is defined by the claims.

According to examples in accordance with an aspect of the invention, there is provided a method of processing captured images from a personal care device, wherein the personal care device comprises: a camera configured, in use, to capture images of one or more features of a user; and vibratory means adapted to vibrate the personal care device so that, in use, the personal care device (and the camera) vibrates, and wherein the method comprises:

processing a captured image from the camera image with an edge detection algorithm to identify a region of the captured image comprising image data having an edge quality value meeting a first predetermined requirement;

extracting image data from the identified region of the captured image; and generating a reconstruction image comprising the extracted image data.

Proposed concepts thus aim to provide schemes, solutions, concepts, designs, methods and systems pertaining to aiding and/or improving image acquisition from a vibratory personal care device having a camera the image of which is influenced by the device vibration. This may either be a camera fixed rigidly to the vibrating device which may then vibrate with the device. Alternatively the camera sensor itself may be situated in a stationary part of a device (e.g. a brush handle) whilst the optical system of the device (like an optical fiber, the imaging lens of the optical system) are subject to the device vibrations. In particular, embodiments of the invention propose identifying image data captured during a target part (e.g. low velocity/motion part) of the vibration cycle based on an assessment of edge quality within the image. Using the identified image data, an image of improved quality may then be constructed. Thus, through adaptation of image data acquisition according to luminance or contrast value, improved images (e.g. images exhibiting less blur and/or distortion) may be constructed/generated. In this way, improved images may be obtained from a vibratory personal care device.

In particular, it is proposed that, to reduce or minimize distortions in images acquired from a camera having an optical path that passes through a vibratory portion of a vibrating personal care device (in use), image data acquisition may be adapted based on the vibration cycle. For instance, image data may be identified for extraction and use based on its edge quality, thus ensuring that only image data captured during a preferred or optimal part of the vibration cycle is used to generate a reconstruction image.

It has been realized that as a vibratory portion of the personal care device changes direction/angle, a period of low or no speed/motion/velocity is present, causing areas of captured images to be clearer and sharper. By detecting image data captured during these periods based on the luminosity or contrast values of the captured image data, image data extraction can be adapted to favor these (e.g. synchronize with) these repeating periods of low speed or low motion. Extracted image data acquired from the periods of low motion can then be used to construct a high quality image (in terms of reduced blur and/or distortion), thus facilitating improved oral/dental care decision making.

In other words, embodiments propose to control the processing of image data from images captured by the camera of a personal care device, wherein the control is based on an edge quality value of the image data. By controlling the processing such that image data is employed only if its edge quality value meets a predetermined requirement, images of improved quality may be generated. Embodiments may therefore facilitate stable and high-quality image acquisition during tooth brushing. Such embodiments may be particularly relevant to teledentistry propositions, for example, by enabling improved imaging of a user's tooth, gum, tongue, etc. For instance, images obtained by proposed embodiments may aid dental care treatments and/or decision making. Accordingly, embodiments may be used in relation to dental treatment selection so as support a dental care professional when selecting treatment for a subject.

Further, embodiments may facilitate image-based diagnostics, superior location sensing, therapy planning (e.g. orthodontics, aligners) and/or dental treatment monitoring.

By being integrated into the normal brushing regimen of a user (instead of using separate devices such as smart phones, dental endo-scopes or handheld intraoral scanners), embodiments may support improved dental care. Improved image-based dental care may therefore be provided by proposed concepts.

Embodiments may, however, be applicable to other vibratory personal care devices, such as shavers, skin cleansing devices, and the like.

Embodiments may therefore provide the advantage that decision making in selecting a care treatment can be improved through the use of images captured by a vibratory personal care device. For example, embodiments may enable a larger number of oral care treatment options to be available (e.g. through the provision of more and/or improved information about a subject's oral health).

Some embodiments may, for example, further comprise the preceding steps of: pre-processing the captured image with an image quality assessment algorithm to determine in image quality value; and preventing processing of the captured image with the edge detection algorithm if the determined image quality value does not meet a predetermined quality requirement. In this way, a check that the captured image is of a minimum required quality (e.g. in terms of blur, distortion, contract, or edge quality) before further processing proceeds. Unwarranted or unnecessary processing or resource usage may thus be avoided for low quality, for example. For instance, if the captured images comprises a line of image data with poor/low edge quality, and the one or more adjacent line are then also found to comprise image data with poor/low edge quality second, it may be determined that there is little to no reason to undertake further processing of the image.

Another embodiment may further comprise obtaining, as a reference image, an image captured by the camera. The first predetermined requirement may then require that the edge quality value of the image data of the identified region is greater than an edge quality value of image data of a corresponding region of the reference image. In this way, a starting/initial image may be used for the purpose of reference or comparison. The edge quality of the image data of a region of the captured image may then be easily compared with that of a corresponding region of the reconstruction image. The result of the comparison then enables a determination to be made as to whether or not to extract (i.e. use) the image data of that region of the captured image. Relatively simple and straight-forward image data comparison techniques may therefore be employed by embodiments to control the use of image data from images captured by the camera.

In another example, the first predetermined requirement may require that the edge quality value of the image data of the identified region is greater than a predetermined edge quality threshold value. Comparison with a single value (rather than that of another image) may thus be employed. Simple comparison techniques/algorithms may therefore be employed. Also, use of a single threshold value may support simple and easy alteration of the requirement.

The step of generating the reconstruction image may comprise storing the extracted image data from the identified region in a corresponding region of the reconstruction image.

Also, some embodiments may comprise storing the extracted image data from the identified region in a corresponding region of the reference image. In this way, the reference image may be updated and/or refine with image data having an improved edge quality value. In some embodiments, processing the captured image may comprise:

- processing a segment (e.g. a row or column) of the captured image with the edge detection algorithm to determine an edge quality value of the image data of the segment;
- comparing the determined edge quality value of the image data of the segment with the first predetermined requirement; and
- based on the comparison result, identifying the segment as a region of the captured image comprising image data having an edge quality value meeting the first predetermined requirement. The result of the comparison enables a determination to be made as to whether or not to extract (i.e. use) the image data of that segment of the captured image. Simple comparison of edge quality may thus be employed by proposed embodiments, thereby facilitate low cost and/or complexity implementations.

The segment of the captured image may, for example, comprise a row or column of the captured image. That is, the image data of the captured image may be deconstructed into segments that correspond to one or more rows or columns. This may reduce a processing burden for example. It is, however, noted that segments may comprise other size, sections and/or shapes of image data of the captured image.

According to yet another aspect of the invention, there is provided a computer program comprising computer program code means which is adapted, when said computer program is run on a computer, to implement a method according to proposed embodiment.

Thus, there may also be provided a computer system comprising: a computer program product according to proposed embodiment; and one or more processors adapted to perform a method according to a proposed concept by execution of the computer-readable program code of said computer program product.

According to another aspect of the invention, there is provided a system for processing captured images from a personal care device, wherein the personal care device comprises: a camera configured, in use, to capture images of one or more features of a user; and vibratory means adapted to vibrate the personal care device so that, in use, the personal care device (and the camera) vibrates. The system comprises:

- a processor arrangement configured to process a captured image from the camera with an edge detection algorithm to identify a region of the captured image comprising image data having an edge quality value meeting a first predetermined requirement; and
- an image processor configured to extract image data from the identified region of the captured image and to generate a reconstruction image comprising the extracted image data.

Such a system may be provided as a standalone system for use with one or more personal care devices. Thus, a system according to an embodiment may be employed with a conventional vibratory personal care device to provided improved and/or extended functionality.

According to another aspect of the invention, there is provided a personal care device comprising:

- vibratory means adapted to vibrate the personal care device so that, in use, the personal care device vibrates with a vibration cycle having a vibration frequency;

- a camera adapted, in use, to capture images of one or more features of a user; and
- a system for processing captured images according to a proposed embodiment.

The personal care device may comprise a toothbrush, and may preferably comprise an electric toothbrush that is adapted to vibrate in use. In other embodiments, the personal care device may comprise a mouthpiece that is adapted to vibrate in use. One or more proposed concept(s) may therefore be employed in a range of different personal care devices. Embodiments may therefore have wide application in the field of personal care devices (and image capture and/or processing concepts for images captured by vibratory personal care devices).

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which.

DETAILED DESCRIPTION OF THE EMBODIMENTS

Figure 1:
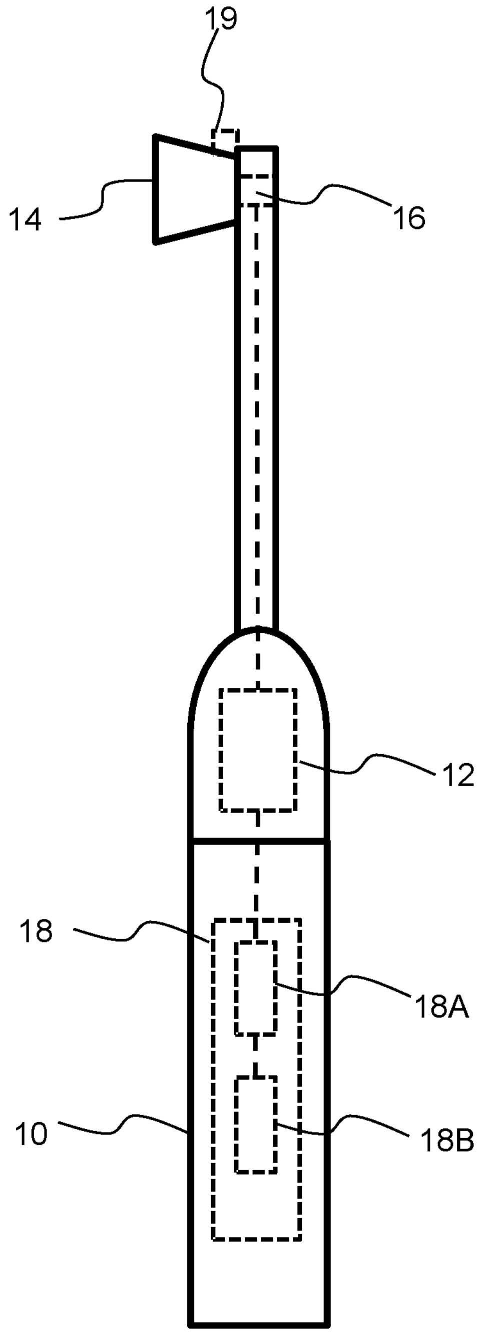
FIG. 1 is a simplified schematic block diagram of an electric toothbrush according to a proposed embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. The mere fact that certain measures are recited in mutually different dependent claims does not indicate that a combination of these measures cannot be used to advantage.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

It should be understood that the Figures are merely schematic and are not drawn to scale. It should also be understood that the same reference numerals are used throughout the Figures to indicate the same or similar parts.

The invention proposes concepts for aiding and/or improving image acquisition from a vibratory personal care device having a camera which vibrates with the device. In particular, embodiments may provide a system, device and/or method which identifies image data captured during a target part (e.g. low velocity/motion part) of the vibration cycle based on edge quality value of the image data. Control of the extraction or further processing of image data from captured images may then be undertaken according to the identified image data. Through such control of the image data acquisition, improved images (e.g. images exhibiting less blur and/or distortion) may be obtained.

In particular, it is proposed that, to reduce or minimize distortions in images acquired from a vibrating personal care device, the acquisition of image data may be adapted according to the vibration cycle of the vibrating personal care device (in use). More specifically, it has been realized that one or more parts of the vibration cycle may be better suited to image capture, for example due to exhibiting reduced motion/movement. It has further been realized that the timing(s) of such a part of the vibration cycle preferred (or optimal) for image capture may be determined based on an edge quality value of captured image data.

Simple assessment of edge quality within captured images may thus be employed to determine preferred, optimal or target image data for use in generating a high quality image exhibiting reduced blur and/or distortion.

In other words, embodiments propose to adapt image data acquisition to the vibration of the personal care device, so as to provide images of improved quality.

Embodiments may therefore facilitate stable and high-quality image acquisition during tooth brushing. Such embodiments may be particularly relevant to teledentistry propositions, for example, by enabling improved imaging of a user's tooth, gum, tongue, etc. For instance, images obtained by proposed embodiments may aid dental care treatments and/or decision making. Accordingly, embodiments may be used in relation to dental treatment selection so as support a dental care professional when selecting treatment for a subject.

Referring to FIG. 1, there is shown a simplified schematic block diagram of an electric toothbrush 10 according to a proposed embodiment. The electric toothbrush 10 comprises vibratory means 12 (specifically, a motor) that is adapted, in use, to vibrate a brush head 14 of the electric toothbrush 10 (with a frequency of about 200 Hz).

The electric toothbrush 10 also comprises a camera 16 (e.g. digital camera) that is adapted, in use, to capture images of one or more oral features of a user.

More specifically, the motor 12 is configured to cause the brush head 14 to repeatedly rotate clockwise then anti-clockwise by around 10°-25° from a rest position in a periodic manner. In this way, the brush head 14 and also the camera vibrates with a periodic vibration waveform.

Figure 2:
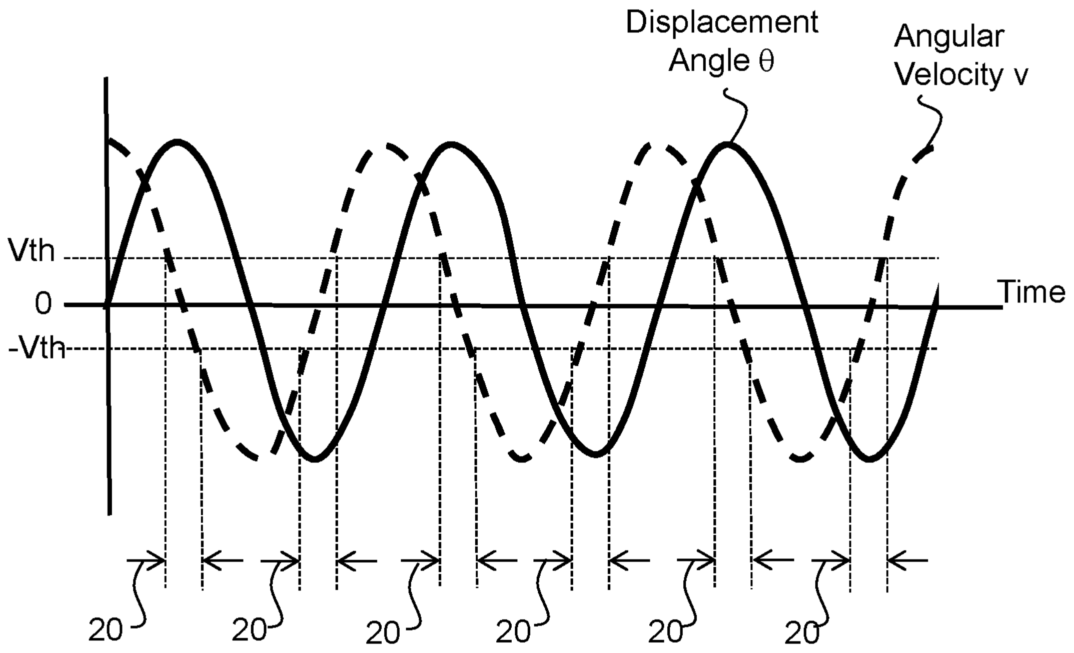
FIG. 2 is a graph showing an exemplary variation in angle θ (of displacement) and angular velocity of the brush head of FIG. 1 over time as the brush head vibrates, wherein the variation in displacement angle θ of the brush head is depicted by the solid line, and wherein the variation in angular velocity v of the brush head is depicted by the dashed line.

By way of further illustration, FIG. 2 depicts a graph showing an exemplary variation in angle θ (of displacement) and angular velocity of the brush head 14 over time as the brush head 14 vibrates. The variation in displacement angle θ of the brush head 14 is depicted by the solid line, whereas the variation in angular velocity v of the brush head 14 is depicted by the dashed line.

It is seen from the variations depicted in FIG. 2 that 'low speed' periods 20, i.e. time periods wherein the magnitude of angular velocity v of the brush head 14 is below a threshold value Vth, can be identified. More specifically, it is seen that, when the magnitude of the displacement angle θ reaches a maximum value, such that the gradient of displacement angle θ variation changes polarity (i.e. when the solid line changes direction), the angular velocity v of the brush head 14 is near-zero. It is proposed that these low speed periods 20 provide the most appropriate opportunities for image capture using a camera that may have limited speed and exposure tuning capabilities. Accordingly, embodiments are based on the concept(s) that the timing of data acquisition may be adapted according to the vibration cycle of the brush head 14. That is, embodiments propose to adapt image acquisition to the vibration of the personal care device, so as to provide images of improved quality.

Referring back to the embodiment of FIG. 1, the electric toothbrush 10 comprises a system 18 for processing captured images. The system comprises a processor arrangement 18A (that may be at least partially distributed across a cloud processing environment for example) that is configured to process a captured image from the camera with an edge detection algorithm to identify a region of the captured image comprising image data having an edge quality value meeting a first predetermined requirement. The system also comprises an image processor 18B that is to extract image data from the identified region of the captured image and to generate a reconstruction image comprising the extracted image data.

Specifically, the processor arrangement 18A obtains an initial reconstruction (e.g. a reference image or a previously captured images). The processor arrangement 18A then processes a segment of the captured image with the edge detection algorithm to determine an edge quality value of the image data of the segment. The processor arrangement 18A then compares the edge quality value of the image data of the segment with an edge quality value of image data of a corresponding region of the initial reconstruction image. Based on the comparison result, the processor arrangement 18A determines whether or not to identify the segment as a region of the captured image comprising image data having an edge quality value meeting the first predetermined requirement.

For instance, the first predetermined requirement may be that the edge quality value of the image data of the identified region is greater than an edge quality value of image data of a corresponding region of the reference image. If the edge quality value of the image data of the identified region is greater than an edge quality value of image data of a corresponding region of the reference image, the processor arrangement 18A identifies the region as a region of the captured image that meets the first predetermined requirement. In such an instance, the processor arrangement 18A is configured to identify regions of captured images having a higher edge quality value than that of a corresponding region of the reference image. Due to the improved (i.e. higher) edge quality, these regions are inferred to contain image data captured during the low speed periods 20 in the vibration cycle. The image processor 18B is then adapted to extract image data from the identified region(s) of the captured image. The system 18 is thus adapted to favor or synchronize image data acquisition with the low speed periods 20, thereby reducing an amount of movement in the acquired image data (which may otherwise cause blurring and/or distortion in a captured image).

Accordingly, it is proposed that the edge quality values of a captured image can be analyzed to determine, by comparison with the reconstruction image, a preferred, optimal or target region of image data for acquisition.

Purely by way of example, edges can be detected using a known edge detection algorithms like a kernel array multiplication with defined "edge values" like Prewitt or Sobel filters (detailed below respectively).

| | | | | | | |
|---|---|---|---|---|---|---|
| Prewitt | −1 | −1 | −1 | −1 | 0 | 1 |
| | 0 | 0 | 0 | −1 | 0 | 1 |
| | 1 | 1 | 1 | −1 | 0 | 1 |
| Sobel | −1 | −2 | −1 | −1 | 0 | 1 |
| | 0 | 0 | 0 | −2 | 0 | 2 |
| | 1 | 2 | 1 | −1 | 0 | 1 |

For such cases, a histogram of the edges detected and taking the mean and standard deviation may be used for an edge quality indicator (i.e. edge quality value) for the proposed concept(s) of identifying image data captured during periods of low or no speed/velocity in the vibration cycle.

To aid reduction in the exposure duration that is required to capture an adequately exposed image, the camera 16 of the embodiment of FIG. 1 comprises an illumination device 19 (e.g. LED) that is configured, in use, to illuminate a part of the user's oral cavity.

Although the embodiment of FIG. 1 has been described as employing a brush head 14 that repeatedly rotates clockwise then anti-clockwise by around 10°-25° from a rest position in a periodic manner, it will be appreciated that other embodiments may employ a brush head that vibrates in a different manner. For instance, alternative embodiments may comprise a brush head that rotates or that shakes (left and right, or up and down) repeatedly, i.e. repeatedly displaces (laterally or vertically) in opposite directions from a rest position. Such embodiments will still exhibit a cyclical vibration pattern having variations in displacement and velocity over time that form periodic waveforms as depicted in FIG. 2, and thus have repeating 'low speed' periods that are identifiable (e.g. via segments of a captured image having higher luminance or contrast).

That is, although the proposed concept(s) have been described above with reference to rotating/angular motion of the vibrating part of the personal care device, the proposed concept(s) may be employed in other vibratory personal care devices exhibiting repetitive vibratory motion.

Also, although the embodiment of FIG. 1 employs a concept of comparing edge quality values of a captured image with those of another image, other embodiments may employ alternative assessments and/or analysis of the edge quality values. For instance, in some embodiments, the processor arrangement 18A may compare the edge quality values of a captured image with a predetermined edge quality threshold value. This edge quality threshold value may be changed or adapted according to one or more preferences or needs (e.g. image quality requirements, processing speed/resources, etc.). The use of a threshold value may support avoidance of processing of segments which—although better than corresponding segments in the reconstruction image-still exhibit very low quality, for example a very low contrast, Referring to FIG. 3, there is shown a simplified schematic block diagram of a mouthpiece 40 according to another embodiment. The mouthpiece 40 is adapted to be inserted into a user's mouth and vibrate (in use) for oral cleaning purposes.

The mouthpiece 40 comprises vibratory means 42 (specifically, an electric motor) that is adapted, in use, to cause the mouthpiece to vibrate with periodic vibration waveform (having a frequency in the range of 100 Hz-500 Hz).

The mouthpiece 40 also comprises a camera 44 positioned in the tray of the mouthpiece whereby it vibrates with the mouthpiece and adapted, in use, to capture images of one or more oral features of the user. A flash LED 46 is also provided in the tray of the mouthpiece for illuminating the oral cavity of the user, in use. The camera 44 and LED 46 are configured to be controlled by a control unit (i.e. controller) 48 of the mouthpiece.

Incorporated with the control unit 48 is a system 49 for processing captured images from the camera 44. The system 49 is configured to identify a region of a captured image comprising image data having an edge quality value meeting a predetermined requirement. The system 50 is configured to extract image data from the identified region of the captured image, and to generate a reconstruction image comprising the extracted image data.

As already explained above with reference to the embodiment of FIG. 1, the system 50 for processing captured images determines regions of captured images that comprise image data captured during a low velocity part of the vibration cycle (e.g. a period of 'low speed/velocity' of the mouthpiece 40, i.e. time period wherein the magnitude of velocity of the mouthpiece 40 is below a predetermined threshold value). The system 50 then controls image data acquisition so that it processes image data that was captured during the target/preferred part of the vibration cycle (e.g. during periods of 'low speed/velocity' of the mouthpiece 40).

It is noted that, in this embodiment, the camera 44 comprises a rolling shutter camera configured to operate at an image capture frame rate. With respect to such a rolling shutter camera, trade-offs in operating characteristics may be required. For example, rolling shutter cameras may be more cost effective (e.g. cheaper) but may take longer for a full image capture depending on the acquisition settings and/or capabilities.

For a rolling shutter camera, the shutter and capture are typically per line, and thus a motion during the capture of all the lines in a captured image will distort the image. However, since an image captured by a rolling shutter camera frame will typically have a high number of lines/rows, a low speed rolling shutter camera will typically still have a fast line/row capturing time. It is proposed that such a line/row capture time will be fast enough to capture sharp, blur free image data during a period of low angular velocity in the vibration cycle. Embodiments therefore propose extracting image data from a captured image that was captured during a preferred/target (e.g. low speed) period of the vibration cycle.

Thus, it will be appreciated that the camera can be free running and out of synchronization with vibration of the personal care device (and thus the image data capture frequency). A full image may then be reconstructed from image data acquired from multiple difference frames of the rolling shutter camera.

Figure 3:
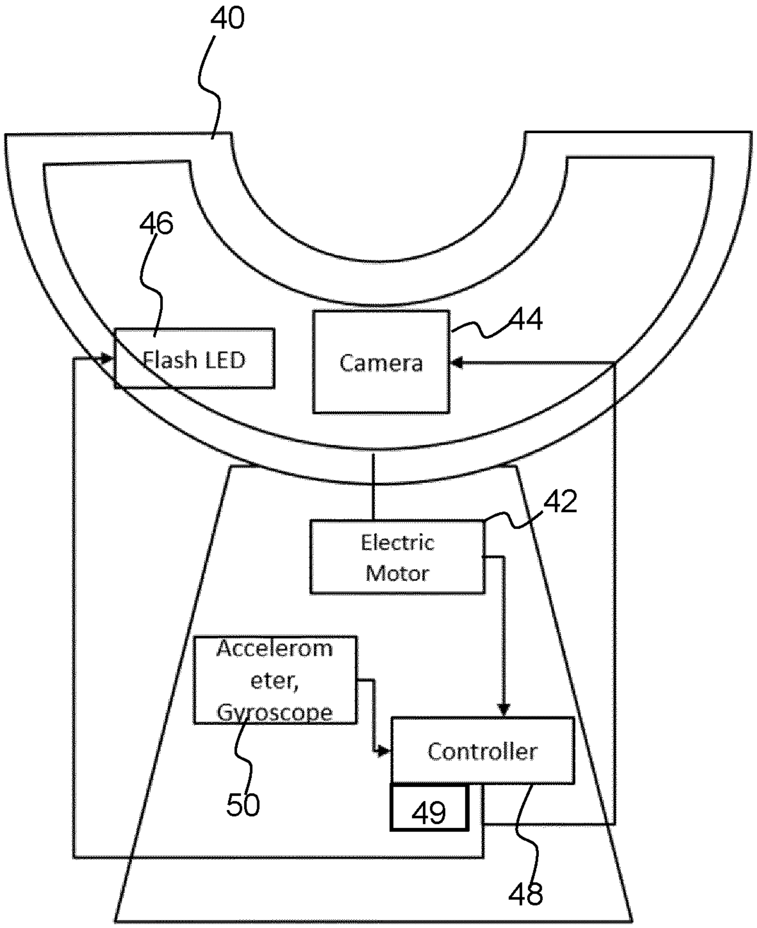
FIG. 3 is a simplified schematic block diagram of a mouthpiece according to a proposed embodiment.
Figure 4:
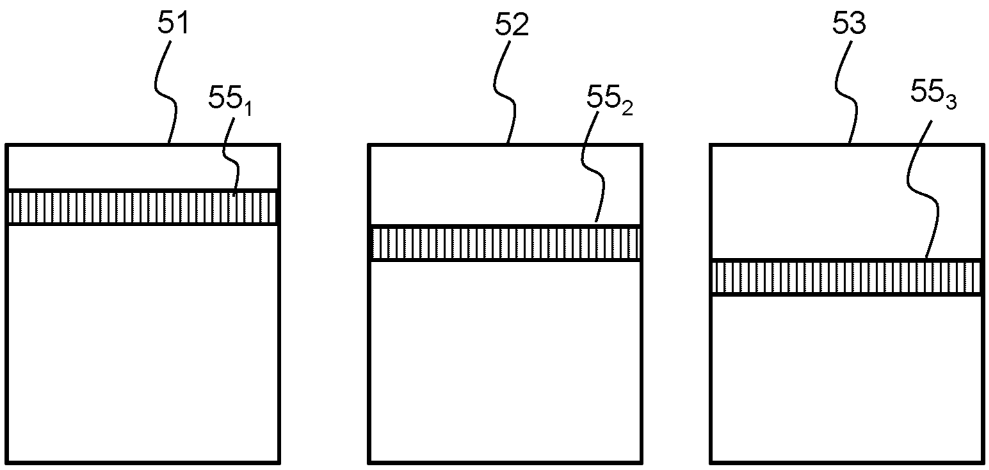
FIG. 4 illustrates extracting image data from captured images according to proposed embodiment.

For example, FIG. 4 provides an illustration of extracting image data from captured images according to a proposed embodiment. The illustration shows first 51, second 52 and third 53 sequentially-captured images from the rolling shutter camera 44 of FIG. 3 (i.e. first to third sequential frames from the rolling shutter camera). The frames comprise first $\mathbf{55}_1$ second $\mathbf{55}_2$ and third $\mathbf{55}_3$ regions, which may e.g. be rows of pixels, which all correspond to the identical segment of the reconstruction image. Here, reference to pixel may encompass a single sensing element of an image sensor or a sensing element (single sensor) of an image sensor array. That is, a pixel may be thought of as being a single element of a sensed image, wherein the sensed image is formed from a plurality of sensed elements (i.e. pixels).

Because the frame rate of the rolling shutter camera differs from the vibration frequency of the personal care device, the first $\mathbf{55}_1$ second $\mathbf{55}_2$ and third $\mathbf{55}_3$ regions are in differing locations within the captured frames of rolling shutter camera. According to the proposed method, the image data of the second $\mathbf{55}_2$ region is compared with the first $\mathbf{55}_1$ region and subsequently the third $\mathbf{55}_3$ region is compared with the second $\mathbf{55}_2$ region.

For example, the first captured region may be captured in a relatively fast motion region where for example the edge quality is relatively low. Subsequently the second captured region may be captured in a relatively low motion region where for example the edge quality is relatively high. Subsequently the third captured region may be captured in a zero motion region where for example the edge quality is even higher than the second region.

According to the proposed method, the image data of the second $\mathbf{55}_2$ region is extracted and replaces the first $\mathbf{55}_1$ region, and subsequently the third $\mathbf{55}_3$ regions is extracted and replaces the second $\mathbf{55}_2$ region, since, based on their edge quality values, they are identified as being captured during progressively superior, lower velocity period of the vibration cycle.

Similar processing methods are applied to all other segments of the image, whereby finally an image comprising the most optimized segments captured at the lowest motion moments is created.

It will therefore be appreciated that embodiments may be configured to (indirectly) identify periods of low device velocity within the vibration cycle (through the identification of image data having a high edge quality). Image data captured during these identified periods may then be extracted and used to construct a single, reconstructed image of improved image quality. That is, by identifying regions of image data with high edge quality, embodiments may synchronize data extraction with the periods of low angular velocity.

By way of yet further explanation, embodiments may be based on a realization that when low or no speed/motion is present, the edge quality is higher.

A reconstruction time for a fully sharp image may be based on the number of sharp regions per captured image and thus have a direct relation to the camera motion, exposure time and capture speed. In an example, there may be 100 sharp lines per frame, where one frame consists of 640 lines. If the framerate of the camera is 30 fps, a full image may be reconstructed from seven sequentially-captured images, resulting in a 7/30 second reconstruction time.

Figure 5:
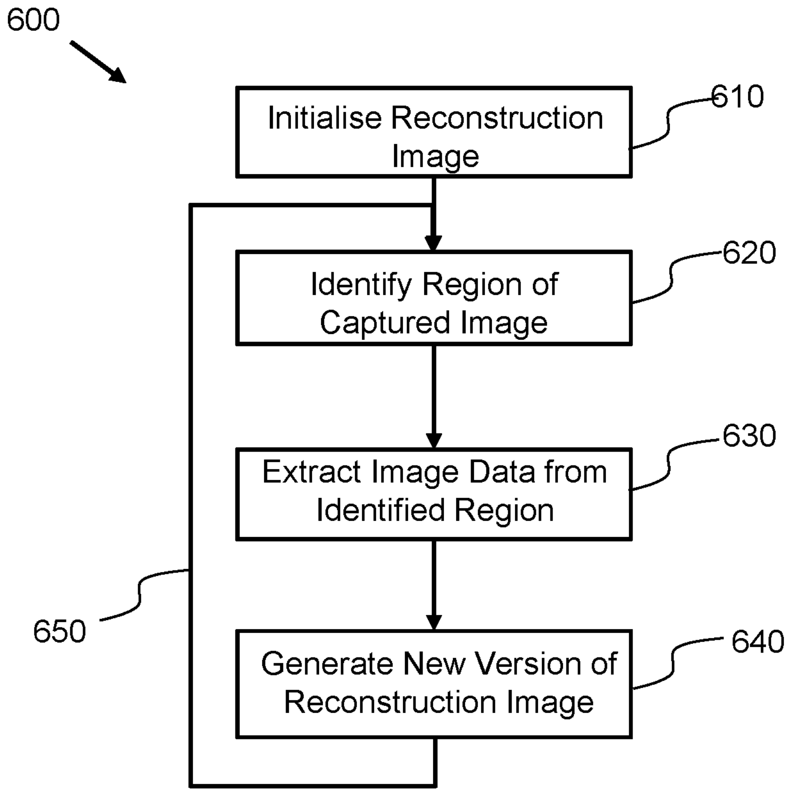
FIG. 5 is a flow diagram of a method of processing captured images from a personal care device according to a proposed embodiment.

By way of example, referring now to FIG. 5, there is depicted a flow diagram of a method 600 of processing captured images from a personal care device according to a proposed embodiment.

For this exemplary embodiment, the personal care device comprises a vibratory means adapted to vibrate the personal care device so that, in use, the personal care device vibrates with a vibration cycle having a vibration. The personal care device also comprises a camera which vibrates with the device, adapted, in use, to capture images of one or more features of a user.

The method 600 begins with the initialization 610 of a reconstruction image. For instance, the reconstruction image may be initialized with a first raw captured image from the camera (e.g. to enforce initial content).

Next, in step 620, a captured image from the camera image is processed with an image processing algorithm to identify a region of the captured image comprising image data having an edge quality value meeting a predetermined requirement. Specifically, the image processing algorithm compares the edge quality of each line of the captured image with that of a corresponding line of the reconstruction image. A line of the captured that has a better edge quality (i.e. has higher edge quality value) than the corresponding line of the reconstruction image is identified as a region meeting the requirement.

Then, image data is extracted from the identified regions in step 630.

In step 640, a new version of the reconstruction image is generated using the extracted data. Specifically, the extracted data is inserted into the corresponding regions/locations of the reconstruction image. In this way, data of the reconstruction image is replaced with sharp, blur-free image data captured during the 'still' (i.e. low velocity) moments in the vibration cycle, thus generating a new and improved version of the reconstruction image.

As indicated by the arrow labelled "650", the process of identifying 620 one or more regions, extracting 630 image data and generating 640 a new version of the reconstruction image can be repeated to generate new versions on the reconstruction image.

It will be appreciated that, in the above described embodiment, the reconstruction image acts as a reference image. With a new and improved version of the reconstruction image being generate, the requirement for a line of the captured image to have a better edge quality value may be made more stringent (i.e. more difficult for corresponding lines in subsequent captured image to exhibit a better edge quality). In this way, the reconstruction image may be continually improved and optimized to contain image data of the highest edge quality.

From the above description of various concepts and embodiments, it will be appreciated that there is proposed a method of processing captured images from a personal care device. Such a method may be employed in a processing system or computer, and such a system/computer may be integrated with a vibratory personal care device.

Figure 6:
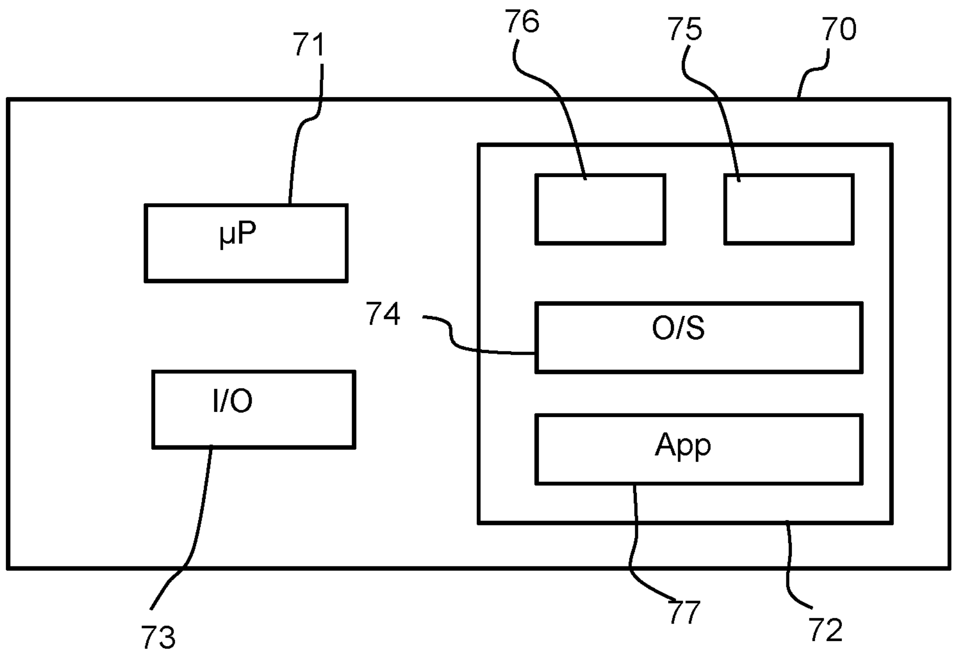
FIG. 6 is a simplified block diagram of a computer within which one or more parts of an embodiment may be employed.

FIG. 6 illustrates an example of a computer 70 within which one or more parts of an embodiment may be employed. Various operations discussed above may utilize the capabilities of the computer 70. For example, one or more parts of a system for providing a subject-specific user interface may be incorporated in any element, module, application, and/or component discussed herein. In this regard, it is to be understood that system functional blocks can run on a single computer or may be distributed over several computers and locations (e.g. connected via internet), such as a cloud-based computing infrastructure.

The computer 70 includes, but is not limited to, PCs, workstations, laptops, PDAs, palm devices, servers, storages, and the like. Generally, in terms of hardware architecture, the computer 70 may include one or more processors 71, memory 72, and one or more I/O devices 73 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 71 is a hardware device for executing software that can be stored in the memory 72. The processor 71 can be virtually any custom made or commercially available processor, a central processing unit (CPU), a digital signal processor (DSP), or an auxiliary processor among several processors associated with the computer 70, and the processor 71 may be a semiconductor based microprocessor (in the form of a microchip) or a microprocessor.

The memory 72 can include any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 72 may incorporate electronic, magnetic, optical, and/or other types of storage media. Note that the memory 72 can have a distributed architecture, where various components are situated remote from one another, but can be accessed by the processor 71.

The software in the memory 72 may include one or more separate programs, each of which comprises an ordered listing of executable instructions for implementing logical functions. The software in the memory 72 includes a suitable operating system (O/S) 74, compiler 76, source code 75, and one or more applications 77 in accordance with exemplary embodiments. As illustrated, the application 77 comprises numerous functional components for implementing the features and operations of the exemplary embodiments. The application 77 of the computer 70 may represent various applications, computational units, logic, functional units, processes, operations, virtual entities, and/or modules in accordance with exemplary embodiments, but the application 77 is not meant to be a limitation.

The operating system 74 controls the execution of other computer programs, and provides scheduling, input-output control, file and data management, memory management, and communication control and related services. It is contemplated by the inventors that the application 77 for implementing exemplary embodiments may be applicable on all commercially available operating systems.

Application 77 may be a source program, executable program (object code), script, or any other entity comprising a set of instructions to be performed. When a source program, then the program is usually translated via a compiler (such as the compiler 76), assembler, interpreter, or the like, which may or may not be included within the memory 72, so as to operate properly in connection with the O/S 74. Furthermore, the application 77 can be written as an object oriented programming language, which has classes of data and methods, or a procedure programming language, which has routines, subroutines, and/or functions, for example but not limited to, C, C++, C#, Pascal, BASIC, API calls, HTML, XHTML, XML, ASP scripts, JavaScript, FORTRAN, COBOL, Perl, Java, ADA, .NET, and the like.

The I/O devices 73 may include input devices such as, for example but not limited to, a mouse, keyboard, scanner, microphone, camera, etc. Furthermore, the I/O devices 73 may also include output devices, for example but not limited to a printer, display, etc. Finally, the I/O devices 73 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 73 also include components for communicating over various networks, such as the Internet or intranet.

If the computer 70 is a PC, workstation, intelligent device or the like, the software in the memory 72 may further include a basic input output system (BIOS) (omitted for simplicity). The BIOS is a set of essential software routines that initialize and test hardware at startup, start the O/S 74, and support the transfer of data among the hardware devices. The BIOS is stored in some type of read-only-memory, such as ROM, PROM, EPROM, EEPROM or the like, so that the BIOS can be executed when the computer 70 is activated.

When the computer 70 is in operation, the processor 71 is configured to execute software stored within the memory 72, to communicate data to and from the memory 72, and to generally control operations of the computer 70 pursuant to the software. The application 77 and the O/S 74 are read, in whole or in part, by the processor 71, perhaps buffered within the processor 71, and then executed.

When the application 77 is implemented in software it should be noted that the application 77 can be stored on virtually any computer readable medium for use by or in connection with any computer related system or method. In the context of this document, a computer readable medium may be an electronic, magnetic, optical, or other physical device or means that can contain or store a computer program for use by or in connection with a computer related system or method.

The application 77 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The computer readable medium can be, for example but not limited to, an electronic, magnetic, optical, electromagnetic, infrared, or semiconductor system, apparatus, device, or propagation medium.

The proposed image capture and/or processing methods, may be implemented in hardware or software, or a mixture of both (for example, as firmware running on a hardware device). To the extent that an embodiment is implemented partly or wholly in software, the functional steps illustrated in the process flowcharts may be performed by suitably programmed physical computing devices, such as one or more central processing units (CPUs) or graphics processing units (GPUs). Each process—and its individual component steps as illustrated in the flowcharts—may be performed by the same or different computing devices. According to embodiments, a computer-readable storage medium stores a computer program comprising computer program code configured to cause one or more physical computing devices to carry out an encoding or decoding method as described above when the program is run on the one or more physical computing devices.

Storage media may include volatile and non-volatile computer memory such as RAM, PROM, EPROM, and EEPROM, optical discs (like CD, DVD, BD), magnetic storage media (like hard discs and tapes). Various storage media may be fixed within a computing device or may be transportable, such that the one or more programs stored thereon can be loaded into a processor.

To the extent that an embodiment is implemented partly or wholly in hardware, the blocks shown in the block diagrams of FIGS. 1 and 3 may be separate physical components, or logical subdivisions of single physical components, or may be all implemented in an integrated manner in one physical component. The functions of one block shown in the drawings may be divided between multiple components in an implementation, or the functions of multiple blocks shown in the drawings may be combined in single components in an implementation. Hardware components suitable for use in embodiments of the present invention include, but are not limited to, conventional microprocessors, application specific integrated circuits (ASICs), and field-programmable gate arrays (FPGAs). One or more blocks may be implemented as a combination of dedicated hardware to perform some functions and one or more programmed microprocessors and associated circuitry to perform other functions.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. If a computer program is discussed above, it may be stored/distributed on a suitable medium, such as an optical storage medium or a solid-state medium supplied together with or as part of other hardware, but may also be distributed in other forms, such as via the Internet or other wired or wireless telecommunication systems. If the term "adapted to" is used in the claims or description, it is noted the term "adapted to" is intended to be equivalent to the term "configured to". Any reference signs in the claims should not be construed as limiting the scope.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method of processing captured images from a personal care device, wherein the personal care device comprises: a camera configured, in use, to capture images of one or more features of a user; and a vibrator adapted to vibrate the personal care device so that, in use, the personal care device vibrates, and wherein the method comprises:

processing a captured image from the camera image with an edge detection algorithm to identify a region of the captured image comprising image data having an edge quality value meeting a first predetermined requirement;

extracting image data from the identified region of the captured image; and generating a reconstruction image comprising the extracted image data;

wherein the processing comprises processing a segment of the captured image with the edge detection algorithm to determine an edge quality value of the image data of the segment;

comparing the determined edge quality value of the image data of the segment with the first predetermined requirement; and based on the comparison result, identifying the segment as a region of the captured image comprising image data having an edge quality value meeting the first predetermined requirement.

2. The method of claim 1, wherein the personal care device comprises an oral care device, and wherein the camera is configured, in use, to capture images of one or more oral features of the user.

3. The method of claim 1, further comprising the step of obtaining, as a reference image, an image captured by the camera, and wherein the first predetermined requirement is that the edge quality value of the image data of the identified region is greater than an edge quality value of image data of a corresponding region of the reference image.

4. The method of claim 3, further comprising replacing image data of the reference image with image data of the reconstruction image.

5. The method of claim 3, further comprising storing the extracted image data from the identified region in a corresponding region of the reference image.

6. The method of claim 1, wherein the first predetermined requirement is that the edge quality value of the image data of the identified region is greater than a predetermined edge quality threshold value.

7. The method of claim 1, wherein the segment of the captured image comprises a row or column of the captured image.

8. The method of claim 1, wherein generating the reconstruction image comprises:

storing the extracted image data from the identified region in a corresponding region of the reconstruction image.

9. A computer program comprising computer program code which is adapted to implement the method of claim 1.

* * * * *